(12) United States Patent
Akahori (10) Patent No.: US 9,380,985 B2
(45) Date of Patent: Jul. 5, 2016

(54) X-RAY TOMOSYNTHESIS IMAGING DEVICE AND CALIBRATION METHOD OF AN X-RAY TOMOSYNTHESIS IMAGING DEVICE

(71) Applicant: FUJIFILM Corporation, Tokyo (JP)

(72) Inventor: Sadato Akahori, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 248 days.

(21) Appl. No.: 14/147,113

(22) Filed: Jan. 3, 2014

(65) Prior Publication Data
US 2014/0119500 A1    May 1, 2014

Related U.S. Application Data

(63) Continuation of application No. PCT/JP2012/067336, filed on Jul. 6, 2012.

(30) Foreign Application Priority Data

Jul. 6, 2011    (JP) .................................. 2011-149912
Jul. 12, 2011   (JP) .................................. 2011-153815

(51) Int. Cl.
| | | |
|---|---|---|
| A61B 6/03 | (2006.01) | |
| A61B 6/02 | (2006.01) | |
| A61B 6/00 | (2006.01) | |
| A61B 6/04 | (2006.01) | |
| G06T 11/00 | (2006.01) | |
| G06T 7/20 | (2006.01) | |

(Continued)

(52) U.S. Cl.
CPC .................. *A61B 6/032* (2013.01); *A61B 6/025* (2013.01); *A61B 6/0492* (2013.01);
(Continued)

(58) Field of Classification Search
USPC ................................................... 378/17, 207
See application file for complete search history.

(56) References Cited

U.S. PATENT DOCUMENTS 4,629,313 A * 12/1986 Tanimoto ................ G03F 7/706
355/53
5,442,445 A *  8/1995 Tatsuno ................ G03F 9/7088
356/401

(Continued)

FOREIGN PATENT DOCUMENTS

DE    10 2008 037 479 A1    6/2009
JP       2000-278606 A      10/2000

(Continued)

OTHER PUBLICATIONS

Extended European Search Report, dated Mar. 5, 2015, in related application No. EP12807484.

(Continued)

*Primary Examiner* — Phillip A Johnston
*Assistant Examiner* — Hsien Tsai
(74) *Attorney, Agent, or Firm* — Birch, Stewart, Kolasch & Birch, LLP (57) ABSTRACT

The X-ray imaging device comprises an X-ray source that is able to move along a predetermined movement path, a movement unit configured to cause the X-ray source to move along the predetermined movement path, an imaging platform that is disposed to face the X-ray source, a flat-panel X-ray detector that is provided to the imaging platform, a marker that is disposed in the imaging platform, a control unit that causes the X-ray source to move and to capture images respectively including the marker from at least two positions, and an image processing unit that calculates a position of an image of the marker in each of the captured images and calculates a slope of a movement axis of the X-ray source with respect to the X-ray detector based on a relative relationship between positions of images of the marker.

19 Claims, 5 Drawing Sheets

(52) U.S. Cl.
CPC .............. *A61B 6/4233* (2013.01); *A61B 6/584* (2013.01); *A61B 6/585* (2013.01); *A61B 6/587* (2013.01); *A61B 6/588* (2013.01); *G06T 7/2033* (2013.01); *G06T 11/005* (2013.01); *A61B 6/4283* (2013.01); *A61B 6/4452* (2013.01); *A61B 6/4464* (2013.01); *A61B 6/502* (2013.01); *G06T 2207/10016* (2013.01); *G06T 2207/10116* (2013.01); *G06T 2207/30004* (2013.01); *G06T 2207/30204* (2013.01); *G06T 2207/30241* (2013.01)

(56) References Cited

U.S. PATENT DOCUMENTS

| | | | |
|---|---|---|---|
| 6,379,043 | B1 | 4/2002 | Zylka et al. |
| 2004/0033426 | A1* | 2/2004 | Den Boef ............... G03B 27/32 430/22 |
| 2007/0122020 | A1 | 5/2007 | Claus et al. |
| 2007/0127622 | A1* | 6/2007 | Main ................... A61N 5/1049 378/64 |
| 2008/0186311 | A1 | 8/2008 | Claus |
| 2010/0310044 | A1 | 12/2010 | Manak et al. |
| 2011/0075795 | A1 | 3/2011 | Akahori |

FOREIGN PATENT DOCUMENTS

| | | |
|---|---|---|
| JP | 2010-252951 A | 11/2010 |
| JP | 2011-67503 A | 4/2011 |
| WO | WO 02/10225 A2 | 12/2002 |

OTHER PUBLICATIONS

International Preliminary Report on Patentability and English translation of the Written Opinion of the International Searching Authority for Application No. PCT/JP2012/067336 dated Jan. 16, 2014 (Forms PCT/IB/338, PCT/IB/373, and PCT/ISA/237).

* cited by examiner

X-RAY TOMOSYNTHESIS IMAGING DEVICE AND CALIBRATION METHOD OF AN X-RAY TOMOSYNTHESIS IMAGING DEVICE

CROSS REFERENCE TO RELATED APPLICATIONS

This non-provisional application is a Continuation of International Application No. PCT/JP2012/067336 filed on Jul. 6, 2012, which claims the benefit of Japanese Application Nos. 2011-149912 and 2011-153815 filed in Japan on Jul. 6, 2011 and Jul. 12, 2011. The entire contents of all of the above applications are hereby incorporated by reference.

BACKGROUND OF THE INVENTION

The present invention relates to an X-ray imaging device that captures an image in a decubitus posture, an upright posture, mammography, or the like and a calibration method therefor, and more particularly, to an X-ray imaging device that can correct a misalignment even when a movement axis of an X-ray source has the misalignment with respect to an X-ray detector, that can obtain a high-precision synthesis image (tomosynthesis image) of a cross section at a predetermined position of a subject, and that furthermore can suppress aging degradation of the misalignment and a calibration method therefor.

Recently, in order to observe an affected part in detail, various X-ray imaging devices that can perform a tomosynthesis imaging operation, in which an image with a desired tomographic plane emphasized can be obtained by irradiating a subject with X-rays from different angles while moving an X-ray source, capturing images, and adding the captured images have been proposed (for example, see JP 2011-67503 A).

In the tomosynthesis imaging, for example, an X-ray source is moved to be parallel to an X-ray detector or to draw an arc of a circle, an ellipse, or the like, plural captured images are obtained by imaging a subject at different irradiation angles, and the captured images are reconstructed to create a tomographic image.

JP 2011-67503 A discloses a radiographic imaging device in which any one of a first mode in which only a radiation source is moved and a second mode in which both the radiation source and detection means are moved can be selected depending on imaging conditions at the time of tomosynthesis imaging and plural captured images are acquired in the selected mode.

However, in the tomosynthesis imaging, precise alignment of a movement axis of the X-ray source with respect to the X-ray detector (X-ray image sensor) is required. Particularly, in an X-ray imaging device using an overhead traveling X-ray source, the X-ray source and the X-ray detector (X-ray image sensor) are not integrated as a unified body and it is thus not easy to install the X-ray source and the X-ray detector with high-precision alignment.

In the conventional tomosynthesis imaging, a method of creating calibration data using a predetermined marker assembly is known. However, this method has difficulties in that it is necessary to manage preciseness of markers, it is necessary to create calibration data for each imaging condition such as an SID (distance between a focal point of an X-ray tube and an image-receiving plane), an angle of an X-ray source, and the number of shots, and the like.

Moreover, in the method of creating calibration data using a predetermined marker assembly, since previously-acquired calibration data is used, there is a problem in that it is not possible to cope with aging degradation (aging variation).

Other than that described above, a method of detecting positional misalignment of an image using a marker and correcting an X-ray image is known (for example, see JP 2000-278606 A).

JP 2000-278606 A discloses an X-ray imaging device in which a supporter having a marker is attached to an imaging region of a subject, a mask image and a live image of the imaging region are captured, an error between the position of the marker in the mask image and the position of the marker in the live image is calculated and subtraction is carried out so as to match both positions with each other, and thereby occurrence of noise in the subtraction image generated due to positional misalignment in a catheterization table is prevented.

Even in this case, there is a problem in that it is necessary to manage preciseness of the marker in order to create calibration data, it is necessary to create calibration data for each imaging condition such as an SID (distance between a focal point of an X-ray tube and an image-receiving plane), an angle of an X-ray source, and the number of shots, and the like.

JP 2010-252951 A discloses X-ray CT equipment that is suitable for use in clinical site and that is intended to acquire a highly precise CT image without a ring artifact. In the X-ray CT equipment disclosed in JP 2010-252951 A, when a ring artifact is detected from an output image, an air calibration data acquiring unit acquires new air calibration data and an air calibration data replacing unit replaces the air calibration data used up to that time point with the new air calibration data.

As described above, JP 2010-252951 A discloses that the air calibration data is replaced, but JP 2010-252951 A relates to X-ray CT equipment. Under the circumstances, an X-ray imaging device that can cope with aging degradation of calibration in tomosynthesis imaging is not known.

SUMMARY OF THE INVENTION

An object of the present invention is to solve the problems based on the conventional techniques and to provide an X-ray imaging device that can correct a misalignment even when a movement axis of an X-ray source has the misalignment with respect to an X-ray detector, that can obtain a high-precision synthesis image (tomosynthesis image) of a cross section at a predetermined position of a subject, and that furthermore can suppress aging degradation of the misalignment in addition to the correction of the misalignment described above and a calibration method therefor.

In order to attain the above described object, a first aspect of the present invention provides an X-ray imaging device comprising: an X-ray source that is able to move along a predetermined movement path; a movement unit configured to cause the X-ray source to move along the predetermined movement path; an imaging platform that is disposed to face the X-ray source; a flat-panel X-ray detector that is provided to the imaging platform; a marker that is disposed in the imaging platform; a control unit that causes the X-ray source to move via the movement unit and to capture images respectively including the marker from at least two positions; and an image processing unit that calculates a position of an image of the marker in each of the captured images and calculates a slope of a movement axis of the X-ray source with respect to the X-ray detector based on a relative relationship between positions of images of the marker.

Preferably, the image processing unit calculates the slope with respect to the X-ray detector for each imaging position of the X-ray source. Preferably, the image processing unit uses the slope with respect to the X-ray detector to reconstruct a tomographic image.

The slope with respect to the X-ray detector is for example a first slope in a plane parallel to a surface of the X-ray detector.

Preferably, the image processing unit further calculates a variation in size of an image of the marker in each of the captured images, calculates a distance between the X-ray source and the X-ray detector using the variation in size, and calculates a second slope in a plane perpendicular to a surface of the X-ray detector as another slope with respect to the X-ray detector.

A second aspect of the present invention provides a calibration method of an X-ray imaging device including an imaging platform disposed to face an X-ray source that is able to move along a predetermined movement path, a flat-panel X-ray detector provided to the imaging platform, and a marker, the calibration method comprising the steps of: causing the X-ray source to move and to capture images respectively including the marker from at least two positions; and calculating a position of an image of the marker in each of the captured images and calculating a slope of a movement axis of the X-ray source with respect to the X-ray detector based on a relative relationship between positions of images of the marker.

Preferably, the slope with respect to the X-ray detector is calculated for each imaging position of the X-ray source.

The slope with respect to the X-ray detector is for example a first slope in a plane parallel to a surface of the X-ray detector.

Preferably, the calibration method further comprises a step of calculating a variation in size of the marker image in each of the captured images, calculating a distance between the X-ray source and the X-ray detector using the variation in size, and calculating a second slope in a plane perpendicular to a surface of the X-ray detector as another slope with respect to the X-ray detector.

A third aspect of the present invention provides an X-ray imaging device comprising: an X-ray source that is able to move along a predetermined movement path; a movement unit configured to cause the X-ray source to move along the predetermined movement path; an imaging platform that is disposed to face the X-ray source; a flat-panel X-ray detector that is provided to the imaging platform; a marker that is disposed in the imaging platform; a calibration unit that performs a calibrating operation on a misalignment in a movement direction of the X-ray source disposed to face the X-ray detector; and a determination unit that determines whether the calibration unit should update calibration data and causes the calibration unit to perform the calibrating operation based on a determination result, wherein an image including the marker is captured by the X-ray source, a position of an image of the marker in the captured image is calculated by the calibration unit, and the determination unit determines whether to update the calibration data based on the position of the image of the marker.

Preferably, the calibration unit causes the X-ray source to move and to capture images respectively including the marker from at least two positions and calculates a position of an image of the marker in each of a first image and a second image among the captured images, and wherein the determination unit calculates a position of a corresponding marker image which corresponds to the marker image in the second image from the position of the image of the marker in the first image using existing calibration data and determines whether to update the calibration data based on a misalignment between the position of the image of the marker in the second image and the position of the corresponding marker image which corresponds to the image of the marker in the second image.

Preferably, the calibration unit causes the X-ray source to move and to capture images respectively including the marker from at least two positions, calculates a position of an image of the marker in each of the captured images, calculates a first slope of a movement axis of the X-ray source in a plane parallel to the surface of the X-ray detector based on a relative relationship between positions of images of the marker, and creates first calibration data based on the first slope.

Preferably, the calibration unit causes the X-ray source to move and to capture images respectively including the marker from at least two positions, calculates a variation in size of an image of the marker in each of the captured images, calculates a distance between the X-ray source and the X-ray detector using the variation in size, calculates a second slope of the X-ray source in a plane perpendicular a the surface of the X-ray detector, and creates second calibration data based on the second slope.

Preferably, the calibration unit calculates at least the first calibration data out of the first calibration data and the second calibration data for each imaging position of the X-ray source.

Preferably, the X-ray imaging device further comprises a reconstruction unit that reconstructs a tomographic image using a plurality of images obtained by causing the X-ray source to move to predetermined imaging positions via the movement unit and performing a tomosynthesis imaging operation, wherein the reconstruction unit uses at least the first calibration data out of the first calibration data and the second calibration data to reconstruct the tomographic image using the plurality of images captured through the tomosynthesis imaging operation.

Preferably, the X-ray imaging device further comprises a notification unit that notifies a determination result of the determination unit on whether to update the calibration data.

A forth aspect of the present invention provides a calibration method of an X-ray imaging device including an imaging platform disposed to face an X-ray source that is able to move along a predetermined movement path, a flat-panel X-ray detector provided to the imaging platform, and a marker, the calibration method comprising the steps of: causing the X-ray source to capture an image including the marker; and calculating a position of an image of the marker in the captured image, determining whether to update calibration data based on the position of the image of the marker, and performing the calibration based on a determination result.

Preferably, the step of performing the calibration includes steps of: causing the X-ray source to move and to capture images respectively including the marker from at least two positions and calculating a position of an image of the marker in each of a first image and a second image among the captured images; calculating a position of a corresponding marker image which corresponds to the image of the marker in the second image from the position of the image of the marker in the first image using existing calibration data; and determining whether to update the calibration data based on a misalignment between the position of the image of the marker in the second image and the position of the corresponding marker image which corresponds to the image of the marker in the second image.

Preferably, the step of performing the calibration includes steps of: causing the X-ray source to move and to capture images respectively including the marker from at least two positions; calculating the position of the image of the marker in each of the captured images; calculating a first slope of a movement axis of the X-ray source in a plane parallel to a surface of the X-ray detector based on a relative relationship between positions of images of the marker; and creating first calibration data based on the first slope.

Preferably, the step of performing the calibration causes the X-ray source to move and to capture images respectively including the marker from at least two positions, calculates a variation in size of an image of the marker in each of the captured images, calculates a distance between the X-ray source and the X-ray detector using the variation in size, calculates a second slope of the X-ray source in a plane perpendicular to a surface of the X-ray detector, and creates second calibration data based on the second slope.

Preferably, at least the first calibration data out of the first calibration data and the second calibration data is calculated for each imaging position of the X-ray source.

According to the present invention, even when the movement axis of the X-ray source has a misalignment with respect to the X-ray detector, it is possible to correct the misalignment. Accordingly, at the time of reconstruction of tomosynthesis, it is possible to perform precise reconstruction using the respective images. As a result, it is possible to obtain a high-precision synthesis image (tomosynthesis image) of a cross section at a predetermined position of a subject.

Moreover, according to the invention, it is possible to easily determine whether it is necessary to update calibration data for correcting the misalignment of the movement axis of the X-ray source with the X-ray detector depending on an aging variation. Accordingly, it is possible to easily see whether to perform calibration and it is thus possible to perform the calibration if necessary. As a result, it is possible to suppress an influence of the aging variation, and it is thus possible to always perform precise reconstruction of tomosynthesis, and to always obtain a high-precision synthesis image (tomosynthesis image) of a cross section at a predetermined position of a subject.

DETAILED DESCRIPTION OF THE INVENTION

Hereinafter, an X-ray imaging device and a calibration method according to the present invention will be described in detail on the basis of exemplary embodiments illustrated in the accompanying drawings.

Figure 1:
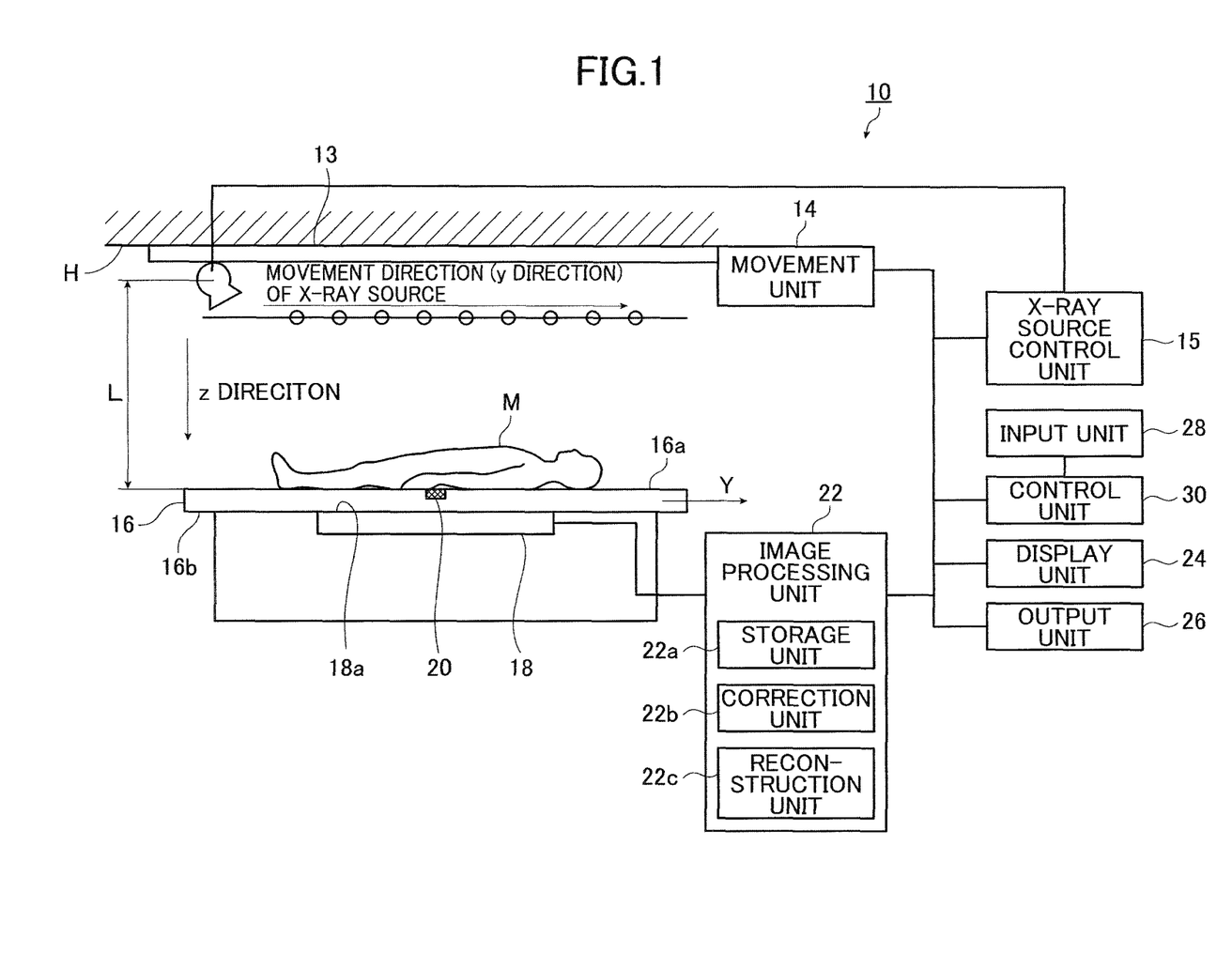
FIG. 1 is a schematic diagram illustrating an X-ray imaging device according to a first embodiment of the present invention.

FIG. 1 is a schematic diagram illustrating an X-ray imaging device according to a first embodiment of the present invention.

The X-ray imaging device 10 according to the first embodiment illustrated in FIG. 1 serves to image a subject M such as a human body in a tomosynthesis manner and to obtain an X-ray tomographic image of a cross section of the subject M at an arbitrary height.

The X-ray imaging device 10 can be used, for example, for tomosynthesis imaging of a decubitus posture, an upright posture, or for mammography.

The X-ray imaging device 10 can employ a built-in X-ray detector 18. When a position of a cassette does not vary before and after calibration, the X-ray imaging device 10 can employ a cassette-type X-ray detector 18.

The X-ray imaging device 10 includes an overhead traveling X-ray source 12, a movement unit 14, an X-ray source control unit 15, an imaging platform 16, an X-ray detector 18, a marker 20, an image processing unit 22, a display unit 24, an output unit 26, an input unit 28 and a control unit 30. The control unit 30 is connected to the movement unit 14, the X-ray source control unit 15, the X-ray detector 18, the image processing unit 22, the display unit 24, the output unit 26, and an input unit 28.

The control unit 30 controls operations of the X-ray imaging device 10 such as an operation of capturing an X-ray image through the use of the X-ray source 12, the movement unit 14, and the X-ray source control unit 15, an image processing operation in the image processing unit 22, a screen displaying operation in the display unit 24, and an outputting operation in the output unit 26, in accordance with an instruction input signal input from the input unit 28.

The input unit 28 is a unit used to input various instructions including an imaging start instruction and a switching instruction to be described later and examples thereof include a mouse and a keyboard. An instruction input is input to the control unit 30 through the input unit 28 and various operations of the X-ray imaging device 10 are performed by the control unit 30. The instruction input from the input unit 28 is displayed, for example, on the display unit 24.

The X-ray source 12 is mounted on a rail 13 disposed on a ceiling H to face the imaging platform 16 so as to be movable.

Figures 2, 3:
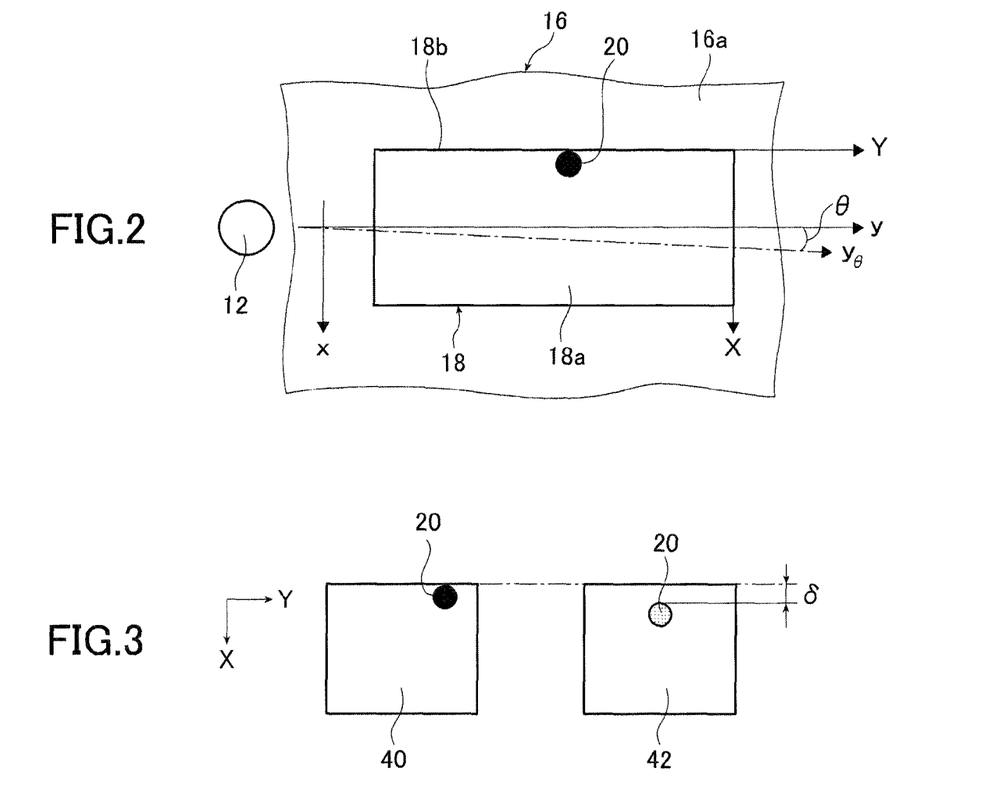
FIG. 2 is a schematic diagram illustrating an arrangement state where an X-ray source and an X-ray detector in the X-ray imaging device according to the first embodiment of the present invention are arranged.
FIG. 3 is a schematic diagram illustrating two images captured by the X-ray imaging device according to the first embodiment of the present invention.

As illustrated in FIG. 2, the rail 13 is disposed so that a movement direction (y direction) of the X-ray source 12 and a length direction (Y direction) of the X-ray detector 18 match with each other, that is, the movement direction (y direction) of the X-ray source 12 and the length direction (Y direction) of the X-ray detector 18 are parallel to each other.

As illustrated in FIG. 1, the rail 13 is provided with a movement unit 14. For example, the movement unit 14 includes a drive unit (not illustrated) such as a stepping motor connected to the X-ray source 12 via a belt (not illustrated), a pulley (not illustrated), and the like. The X-ray source 12 is able to linearly move along the rail 13 and to stop at a predetermined position on the rail 13 through the use of the movement unit 14.

The configuration of the movement unit 14 is not particularly limited as long as it can cause the X-ray source 12 to move along the rail 13 and can cause the X-ray source 12 to stop at a predetermined imaging position.

The movement path of the X-ray source 12 is not limited to a linear path, but may be a circular-arc path. In this case, the rail 13 is disposed in a circular-arc shape.

The X-ray source 12 irradiates a subject M on a surface 16a of the imaging platform 16 with X-rays (radiations) and can change the irradiation angle of X-rays toward the subject M. An X-ray source capable of changing the irradiation angle of X-rays which is typically used for an X-ray imaging device can be used as the X-ray source 12. For example, the X-ray source 12 is provided with a collimator (irradiation field diaphragm) which is not illustrated.

The X-ray source 12 is connected to the X-ray source control unit 15. The irradiation with X-rays and the irradiation angle of X-rays from the X-ray source 12 are controlled by the X-ray source control unit 15. Depending on the imaging conditions, the X-ray source 12 is moved to a predetermined imaging position by the movement unit 14 and the irradiation angle of X-rays toward the subject M is changed by the X-ray source control unit 15, and then, X-rays of a predetermined intensity are irradiated from the X-ray source 12 for a predetermined time. That is, X-rays of a predetermined dose are irradiated from the X-ray source 12 toward the subject M.

A subject M such as a person or an animal lies on the surface 16a of the imaging platform 16. For example, a person lies in a decubitus posture on the surface 16a of the imaging platform 16 as the subject M.

On the rear surface 16b of the imaging platform 16, a flat-type (flat-panel type) X-ray detector 18 (hereinafter, referred to as FPD 18) is disposed to face the rail 13 across the imaging platform 16. In this embodiment, as described above, the length direction (Y direction, see FIG. 2) of the FPD 18 and the length direction of the rail 13, that is, the movement direction (y direction) of the X-ray source 12, are set to be parallel to each other.

The FPD 18 is disposed on the rear surface 16b of the imaging platform 16 with an X-ray-receiving plane directed upward. The FPD 18 detects X-rays passing through the subject M, photoelectrically converts the detected X-rays, and acquires digital image data (projection data) corresponding to a captured X-ray image of the subject M, and has an imaging plane in which plural pixels are arranged in a two-dimensional matrix shape in a detector case. The digital image data is output from the FPD 18 to the image processing unit 22. As described above, the movement direction (y direction) of the X-ray source 12 and the length direction (Y direction) of the FPD 18 are set to be parallel to each other and the movement direction (y direction) of the X-ray source 12 is set to match with the pixel arrangement direction of the FPD 18.

In the present invention, a "slope" means a slope with respect to the arrangement of plural pixels (arrangement direction of the two-dimensional matrix).

Various systems such as a direct system of directly converting X-rays (radiations) into electric charges and an indirect system of temporarily converting X-rays (radiations) into light and additionally converting the converted light into an electrical signal can be used for the FPD 18. The FPD 18 may be configured to be movable in the movement direction of the X-ray source 12.

For example, a marker 20 is disposed in the imaging platform 16 in a region in which the FPD 18 is disposed. The marker 20 is disposed in the imaging platform 16 with a gap from the surface 18a of the FPD 18. The marker 20 may be disposed to match its edge with an outer edge 18b of the FPD 18.

The marker 20 is imaged before performing a tomosynthesis imaging operation on the subject M, for example, at the time of starting up the device, and is used to calibrate plural pieces of captured projection data (X-ray images).

The marker 20 is formed of a material hardly transmitting radiations, such as metals, preferably metals having a large atomic number. A shape from which the center of the marker 20 can be easily seen, such as a shape having a cross hole, can be preferably used as the shape of the marker 20. The number of markers 20 is not particularly limited, and may be two or more. When the number of markers is two or more, it is preferable that the markers have different shapes from one another so as to easily identify the respective markers. When the number of markers 20 is two or more, for example, four markers are disposed. When the number of markers 20 is two or more, the arrangement pattern thereof is not particularly limited and the markers are disposed, for example, in a rectangular shape.

The marker 20 may be detachably attached to the imaging platform 16. In this case, when the marker 20 is appropriately disposed on the imaging platform 16 and is imaged only at the time of calibration, for example, at the time of starting up the device, calibration is possible. In this way, by detachably attaching the marker 20, it is possible to easily perform calibration.

In the X-ray imaging device 10 according to this embodiment, when a tomosynthesis imaging operation is performed, the subject M is irradiated with X-rays at different imaging angles (at constant time intervals) while causing the X-ray source 12 to move in the y direction through the use of the movement unit 14 and changing the irradiation angle of X-rays toward the subject M at a predetermined imaging position. The X-rays emitted from the X-ray source 12 pass through the subject M, are incident on the light-receiving plane of the FPD 18, and are detected and photoelectrically converted by the FPD 18, whereby projection data (digital image data) corresponding to a captured X-ray image of the subject M is acquired.

In case of the tomosynthesis imaging, plural (for example, 20 to 80) X-ray images of the subject M imaged at different angles are captured by one time of imaging operation, and plural pieces of projection data (digital image data) corresponding to the plural captured X-ray images are sequentially output from the FPD 18 to the image processing unit 22 (storage unit 22a).

The image processing unit 22 is a unit configured to receive the projection data of the plural X-ray images acquired by the FPD 18, to perform an image processing operation (such as a correction processing (calibration) and an image synthesis processing) using the projection data of the plural X-ray images, and to reconstruct an X-ray tomographic image of a cross section of the subject M at an arbitrary height. The image processing unit 22 includes a storage unit 22a, a correction unit 22b (calibration unit), and a reconstruction unit 22c.

The storage unit 22a receives the plural pieces of projection data of the X-ray images acquired by the FPD 18 and stores the projection data of the X-ray images.

As will be described later, the storage unit 22a also stores a designed size of the marker 20 in the projection data and a threshold value of a misalignment amount (a shift amount δ).

The correction unit 22b calculates a misalignment amount of position (position information of the X-ray source 12) at each imaging position of the X-ray source 12, and corrects the position information of the X-ray source 12 (position information of an X-ray tube) in the projection data captured at an imaging position having a large misalignment amount when the misalignment amount at that position is larger than a predetermined value (for example, threshold value). That is, the correction unit calculates the misalignment amounts of all the projection data pieces of the X-ray images acquired through the tomosynthesis imaging, and corrects the position information of the X-ray source 12 (position information of the X-ray tube) in the projection data captured at an imaging position having a large misalignment amount when the misalignment amount at that position is larger than a predetermined value (for example, threshold value).

The position information of the X-ray source 12 (position information of the X-ray tube) based on the misalignment amounts of all the projection data pieces may be corrected without setting a threshold value of the misalignment amount.

The position information of the X-ray source 12 (position information of the X-ray tube) is corrected to information close to the actual position of the X-ray source 12 and is used for the reconstruction calculation by correcting the slope of the movement axis of the X-ray source 12 on the basis of a designed value (target value indicating from what positions plural images are captured, respectively). The correction unit 22b has an image recognition function of the marker 20 (marker image).

In this embodiment, the slope of the movement axis of the X-ray source 12 with respect to the FPD 18 (X-ray detector) indicates a misalignment amount of position at an imaging position of the X-ray source 12. For example, the slope is a misalignment amount in the movement direction ($y_\theta$ direction) of the X-ray source 12 with respect to the length direction (Y direction) of the FPD 18 illustrated in FIG. 2. Further, the misalignment amount of position of the X-ray source 12 at the imaging position includes a misalignment amount of a distance between the X-ray source 12 and the surface 18a of the FPD 18 (X-ray source-FPD distance L) as illustrated in FIG. 1.

When a misalignment amount is larger than a predetermined value (for example, a threshold value) and is, for example, a misalignment with respect to the length direction (Y direction) of the FPD 18, on the basis of the misalignment amount of position, the correction unit 22b corrects the imaging position of the X-ray source 12 by a value corresponding to the misalignment amount.

Regarding the misalignment amount of the distance between the X-ray source 12 and the surface 18a of the FPD 18 (the X-ray source-FPD distance L), when the X-ray source-FPD distance L varies from a set distance, the size of the marker 20 (marker image) in the captured image varies. Accordingly, a variation rate, that is, an enlargement rate or a reduction rate, of the marker 20 (marker image) is calculated for the misalignment amount in the X-ray source-FPD distance L and is stored, for example, in the storage unit 22a. By enlarging or reducing the projection data in accordance with the enlargement rate or the reduction rate, the correction unit 22b can correct the misalignment amount in the z direction illustrated in FIG. 1.

Needless to say, the correction unit 22b may correct both the misalignment amount of position and the misalignment amount of distance described above.

The reconstruction unit 22c performs an image synthesis processing on the plural pieces of projection data of the X-ray images including the projection data, which has been subjected to the correction processing if necessary by the correction unit 22b, using the position information of the X-ray source 12 (position information of the X-ray tube) corrected if necessary and reconstructs an X-ray tomographic image of a cross section at an arbitrary height of the subject M.

The image processing unit 22 (the storage unit 22a, the correction unit 22b (calibration unit), and the reconstruction unit 22c) is not limited to hardware (device). For example, it may be implemented by a program causing a computer to perform the processing to be performed on the projection data stored in the storage unit 22a by the correction unit 22b (calibration unit) and the reconstruction unit 22c of the image processing unit 22.

The display unit 24 is a unit used to display contents of an instruction input signal input from the input unit 28 to the control unit 30, an X-ray tomographic image reconstructed by the image processing unit 22 in accordance with the instruction input signal, and the like, and examples thereof include flat-panel displays such as a liquid crystal display.

The output unit 26 is a unit used to output the X-ray tomographic image reconstructed by the image processing unit 22 in accordance with the instruction input signal input from the input unit 28 to the control unit 30, and examples thereof include various printers printing out the X-ray tomographic image and a storage device storing the digital image data of the X-ray tomographic image in various recording media.

In the tomosynthesis imaging using the X-ray imaging device 10 according to this embodiment, as described above, precise alignment of the FPD 18 (X-ray detector 18) and the movement axis of the X-ray source 12 is required. In the X-ray imaging device 10 using the overhead traveling X-ray source 12 as in this embodiment, since the X-ray source 12 and the FPD 18 are not incorporated as a unified body, it is difficult to precisely align the X-ray source 12 and the FPD 18. Accordingly, when the X-ray source 12 moves, the X-ray source 12 may move in the $y_\theta$ direction departing from the length direction (Y direction) of the FPD 18 as illustrated in FIG. 2 and the reconstruction may be performed using the captured images obtained in that state. In this case, a high-precision synthesis image (tomosynthesis image) cannot be obtained.

Therefore, in this embodiment, it is possible to correct the misalignment of the movement direction of the X-ray source 12 with respect to the FPD 18 by performing the calibration as described below.

The calibration method of the X-ray imaging device 10 according to this embodiment will be described below.

First, before performing the tomosynthesis imaging operation on a subject M, for example, at the time of starting up the device, at least two images are captured in such a manner as to respectively include the marker 20 while causing the X-ray source 12 to move in the movement direction (y direction) through the use of the movement unit 14. In this case, for example, as illustrated in FIG. 3, a first image 40 and a second image 42 are obtained.

In this case, if the movement direction (y direction) of the X-ray source 12 is parallel to the length direction (Y direction) of the FPD 18, the position of the marker 20 in the X direction perpendicular to the length direction (Y direction) of the FPD 18 is the same in the first image 40 and the second image 42. On the other hand, if the movement direction (y direction) of the X-ray source 12 departs from the length direction of the FPD 18, the position in the X direction is different by δ between the first image 40 and the second image 42. That is, the position in the X-direction is shifted by δ.

A misalignment angle θ of the X-ray source 12 can be calculated on the basis of the shift amount δ and the distance d between the imaging positions of the first image 40 and the second image 42. That is, the misalignment angle θ can be calculated by $\theta = \tan^{-1}(\delta/d)$.

Figure 4:
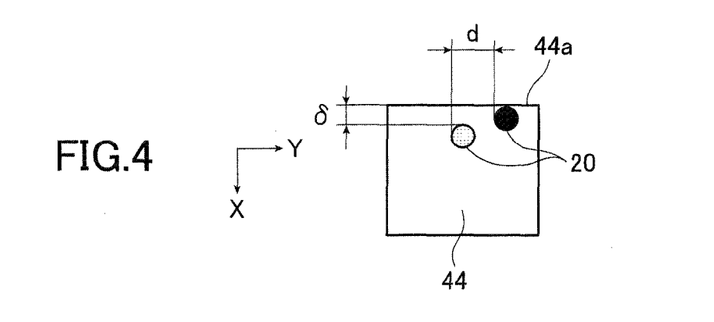
FIG. 4 is a schematic diagram illustrating a synthesis image of two images captured by the X-ray imaging device according to the first embodiment of the present invention.

As illustrated in FIG. 4, the first image 40 and the second image 42 may be synthesized with the edges in the X direction of the captured images fitted to each other to acquire a synthesis image 44, then the shift amount δ may be calculated, and the misalignment angle θ of the X-ray source 12 may be calculated on the basis of the shift amount δ and the distance d between the imaging positions of the first image 40 and the second image 42. In this way, the misalignment angle θ (first slope) of the X-ray source 12 can be calculated using the relative relationship between the positions of the captured images of the marker 20. Reference numeral 44a represents the outer edge of the synthesis image 44.

Here, the misalignment angle θ (first slope) is formed from the above-mentioned slope to the arrangement of plural pixels (arrangement direction of a two-dimensional matrix).

When a tomosynthesis image is acquired using the shift amount δ and the misalignment angle θ of the X-ray source 12, the imaging positions (position information of the X-ray source 12 (position information of the X-ray tube)) of the respective captured images are adjusted and then the tomosynthesis image is reconstructed. Accordingly, it is possible to obtain a high-precision tomosynthesis image. Instead of after adjustment of the positions of the respective captured images using the shift amount δ and the misalignment angle θ of the X-ray source 12, the tomosynthesis image may be reconstructed using the shift amount δ and the misalignment angle θ of the X-ray source 12.

As described above, the relationship between the variation rate of the size of the marker 20 in the captured images and the X-ray source-FPD distance L is obtained in advance and is stored, for example, in the storage unit 22a. Accordingly, even when the marker 20 illustrated in FIG. 5A varies in size to the marker 21 illustrated in FIG. 5B, the X-ray source-FPD distance L is obtained. In this case, the misalignment amount and the misalignment angle of the X-ray source 12 in the plane perpendicular to the surface of the FPD 18, that is, the misalignment amount and the misalignment angle in the z direction illustrated in FIG. 1, can be calculated. In this way, the misalignment angle (second slope) of the X-ray source 12 in the z direction can be calculated using the relative relationship between the positions of the captured images of the marker 20.

When a tomosynthesis image is acquired using the misalignment amount and the misalignment angle of the X-ray source 12 with respect to the surface of the FPD 18, the sizes at the imaging positions (position information of the X-ray source 12 (position information of the X-ray tube)) of the respective captured images are adjusted and then the tomosynthesis image is reconstructed. Accordingly, it is possible to obtain a high-precision tomosynthesis image. Instead of after adjustment of the size of the imaged object in the respective captured images using the misalignment amount and the misalignment angle with respect to the surface of the FPD 18, the tomosynthesis image may be reconstructed using the misalignment amount and the misalignment angle with respect to the surface of the FPD 18.

In this embodiment, the calibration can be performed as described above.

The calculation of the shift amount δ and the misalignment angle θ of the X-ray source 12 and the calculation of the misalignment amount and the misalignment angle in the z direction, that is, the calibration, can be preferably performed in a state where there is no subject M (patient) on the surface 16a of the imaging platform 16, but may be performed in a state where a subject M (patient) is being imaged.

In order to enable the correction when the movement axis of the X-ray source 12 is not straight, that is, when the rail 13 is not parallel to the length direction (Y direction) of the FPD 18, the shift amount δ and the misalignment angle θ of the X-ray source 12 and the misalignment amount and the misalignment angle in the z direction may be calculated for each position of the X-ray source 12, may be stored in the storage unit 22a, for example, in the form of a table, and may be used at the time of tomosynthesis imaging.

The tomosynthesis imaging of the X-ray imaging device 10 will be described below.

First, when an imaging start instruction is given from the input unit 28 after a subject M is positioned on the surface 16a of the imaging platform 16, the tomosynthesis imaging is started under the control of the control unit 30.

When the imaging is started, the subject M is irradiated with X-rays at different irradiation angles while causing the X-ray source 12 to move in the y direction through the use of the movement unit 14 and changing the emitting angle of the X-ray source 12 toward the subject M at a predetermined imaging position, and plural pieces of projection data (X-ray images) having different imaging angles are obtained by one time of imaging operation. Every time an X-ray image of the subject M is captured, the projection data corresponding to the captured X-ray image is output from the FPD 18 to the storage unit 22a of the image processing unit 22 and the plural pieces of projection data of the X-ray images acquired by the FPD 18 are stored in the storage unit 32.

When a position misalignment is present at each imaging position, the correction unit 22b calculates the misalignment amount thereof in advance. The imaging position (position information of the X-ray source 12 (position information of the X-ray tube)) of the projection data having the position misalignment is corrected by the correction unit 22b. The corrected imaging position (position information of the X-ray source 12 (position information of the X-ray tube)) is output to the reconstruction unit 22c.

Then, the reconstruction unit 22c reconstructs an X-ray tomographic image of a cross section of the subject M at an arbitrary height using the projection data and the corrected imaging position (position information of the X-ray source 12 (position information of the X-ray tube)). Since the position misalignment of the imaging position is corrected in this way, it is possible to obtain a high-precision synthesis image (tomosynthesis image) of a cross section of the subject M at a predetermined position.

For example, the obtained tomosynthesis image (X-ray tomographic image) is displayed, for example, in the display unit 24. The tomosynthesis image (X-ray tomographic image) is output to the output unit 26, and the output unit 26, for example, prints out the tomosynthesis image (X-ray tomographic image) and stores the digital image data of the X-ray tomographic image in a recording medium.

Next, the reconstruction of an X-ray tomographic image in the tomosynthesis imaging will be described below.

Figure 6A:
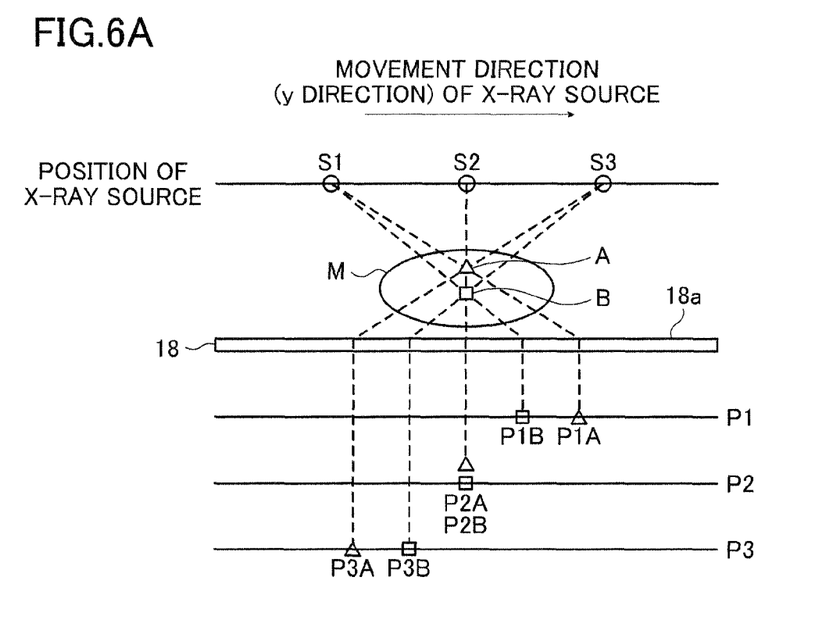
FIGS. 6A and 6B are conceptual diagrams illustrating a state where an X-ray tomographic image captured through tomosynthesis imaging is reconstructed.
Figure 6B:
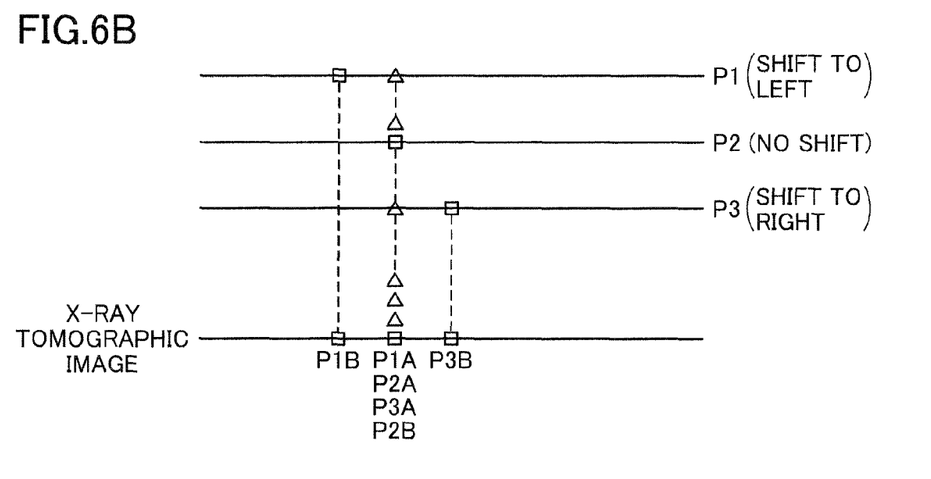

FIGS. 6A and 6B are conceptual diagrams illustrating a state where an X-ray tomographic image captured through the tomosynthesis imaging is reconstructed.

At the time of the tomosynthesis imaging, as illustrated in FIG. 6A, it is assumed that the X-ray source 12 starts from position S1 and moves to position S3, a subject M is irradiated with radiations from source positions S1, S2, and S3, and X-ray images P1, P2, and P3 of the subject M are respectively obtained.

As illustrated in FIG. 6A, it is assumed that imaging targets A and B are present at two positions having different heights in a subject M. At the imaging positions (the position of the X-ray source 12 at the time of imaging) S1, S2, and S3, X-rays irradiated from the X-ray source 12 pass through the subject M and are incident on the FPD 18. As a result, two imaging targets A and B are projected with different positional relationships in the X-ray images P1, P2, and P3 corresponding to the imaging positions S1, S2, and S3.

For example, in case of the X-ray image P1, since the position S1 of the X-ray source 12 is located on the left side of the imaging targets A and B in the movement direction of the X-ray source 12, the imaging targets A and B are projected to positions P1A and P1B shifted to the right side of the imaging targets A and B. Similarly, in case of the X-ray image P2, the imaging targets are projected to positions P2A and P2B just thereunder, and in case of the X-ray image P3, the imaging targets are projected to positions P3A and P3B shifted to the left side.

When the X-ray tomographic image of a cross section at a height at which the imaging target A is present is reconstructed, the X-ray image P1 is shifted to the left and the X-ray image P3 is shifted to the right, for example, as illustrated in FIG. 6B, so that the projection positions P1A, P2A, and P3A of the imaging target A are matched with each other on the basis of the position of the X-ray source 12, and then the X-ray images are combined. Accordingly, the X-ray tomographic image at the height at which the imaging target A is present is reconstructed. Similarly, an X-ray tomographic image of a cross section at an arbitrary height can be reconstructed.

A shift and addition method is representatively used as the method of reconstructing an X-ray tomographic image. In the shift and addition method, the positions of the plural captured projection data pieces (X-ray images) are sequentially shifted and added on the basis of the position of the X-ray source 12 at the time of capturing each X-ray image.

Next, a second embodiment of the present invention will be described below.

Figure 7:
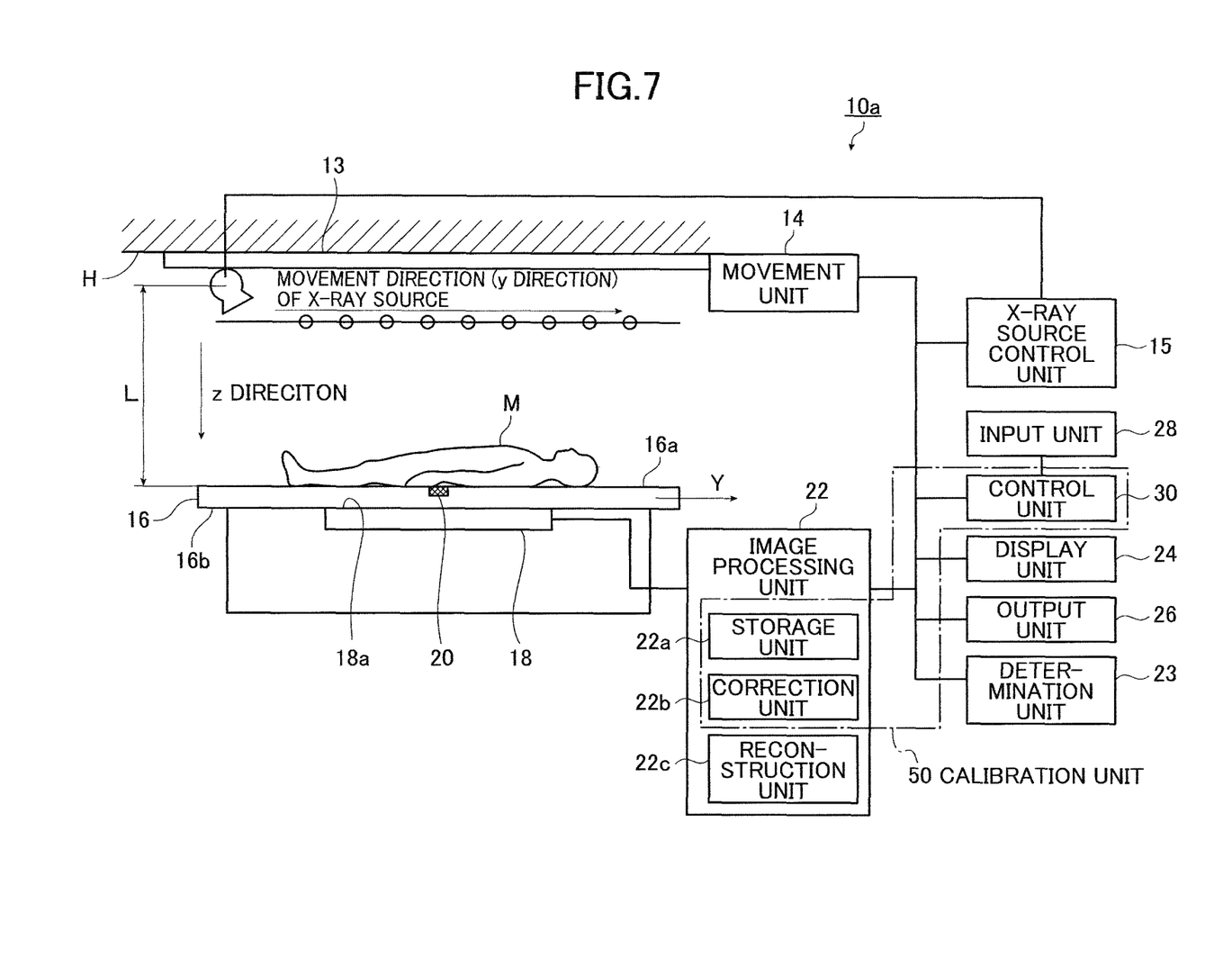
FIG. 7 is a schematic diagram illustrating an X-ray imaging device according to a second embodiment of the present invention.
Figure 8:
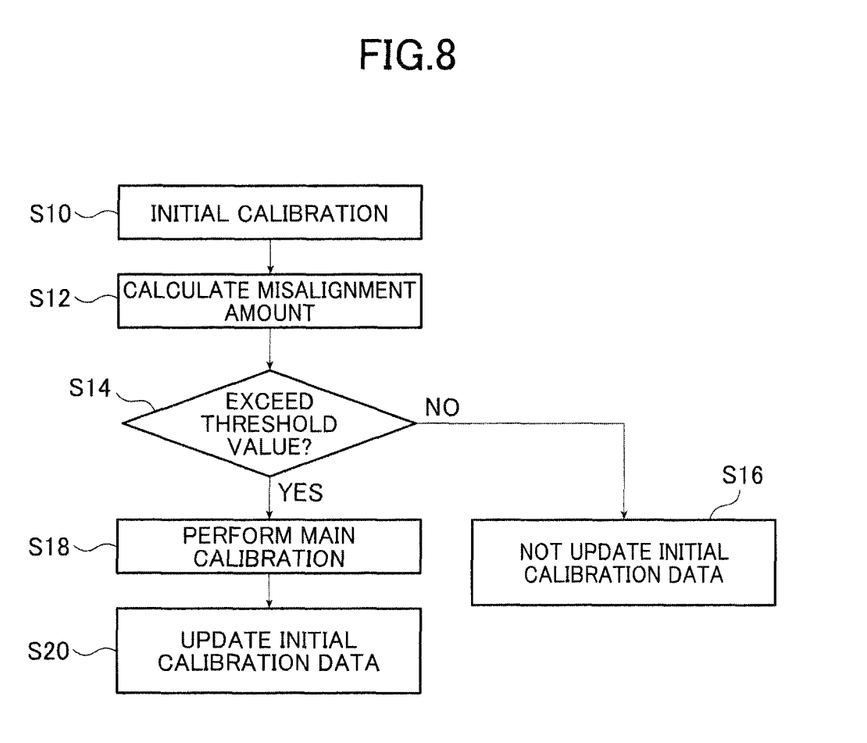
FIG. 8 is a flowchart illustrating a calibration method in the X-ray imaging device according to the second embodiment of the present invention.

FIG. 7 is a schematic diagram illustrating an X-ray imaging device according to the second embodiment of the present invention. FIG. 8 is a flowchart illustrating a calibration method in the X-ray imaging device according to the second embodiment of the present invention.

In this embodiment, the same elements as elements of the first embodiment illustrated in FIGS. 1 to 5 will be referenced by the same reference numerals and detailed description thereof will not be repeated.

The X-ray imaging device 10a according to the second embodiment illustrated in FIG. 7 has the same configuration and operations as the X-ray imaging device 10 according to the first embodiment, except that a determination unit 23 is additionally provided and the operation of the image processing unit 22 and the calibration method are different in comparison with the X-ray imaging device 10 according to the first embodiment illustrated in FIG. 1, and thus detailed description thereof will not be repeated.

In the X-ray imaging device 10a according to this embodiment, the determination unit 23 is connected to the control unit 30.

The control unit 30 controls operations of the X-ray imaging device 10a such as an operation of capturing an X-ray image through the use of the X-ray source 12, the movement unit 14, and the X-ray source control unit 15, an image processing operation in the image processing unit 22, an operation of the determination unit 23 of determining whether to update calibration data, a screen displaying operation in the display unit 24, and an outputting operation in the output unit 26, in accordance with an instruction input signal input from the input unit 28.

On the basis of the determination result of the determination unit 23, at least first calibration data out of the first calibration data and second calibration data to be described later is created by the image processing unit 22 (correction unit 22b to be described later) under the control of the control unit 30, and the created calibration data is stored in the image processing unit 22 (storage unit 22a to be described later).

In this embodiment, the calibration unit 50 is constituted by the storage unit 22a, the correction unit 22b, and the control unit 30.

The determination unit 23 determines whether the calibration unit 50 should update calibration data. The determination unit 23 determines whether to update the calibration data on the basis of at least the position of the marker 20 (marker image) in the captured image out of the position of the marker 20 (marker image) in the captured image obtained by the calibration unit 50 and the size of the marker 20 (marker image) in the captured image as will be described later. That is, the determination unit 23 determines whether to cause the calibration unit 50 to perform a calibration operation and to update the calibration data previously stored in the storage unit 22a.

The determination unit 23 also calculates the position of a corresponding image of a marker which corresponds to the image of the marker 20 in the second image 42 using the first calibration data currently stored. The determination unit also calculates the size of the corresponding image of the marker which corresponds to the image of the marker 20 in the second image 42 using the second calibration data currently stored.

In this embodiment, for example, one marker 20 is disposed in the imaging platform 16 in an area in which the FPD 18 is disposed as in the first embodiment. The marker 20 is disposed with its edge matched with the outer edge 18b of the FPD 18. The marker 20 is disposed in the imaging platform 16 with a gap from the surface 18a of the FPD 18.

The marker 20 may be detachably attached to the imaging platform 16. In this way, by detachably attaching the marker 20, it is possible to easily update the calibration data.

Next, the constituent units of the image processing unit 22 will be described below in detail.

The storage unit 22a receives plural projection data pieces of X-ray images acquired by the FPD 18 and stores the projection data pieces of the X-ray images.

The storage unit 22a also stores a designed size of the marker 20 in the projection data, and threshold values for determining the degree of coincidence between the positions of the images of the marker 20 to be described later and for determining the degree of coincidence between the sizes of the images of the marker 20 to be described later.

Moreover, the storage unit 22a stores the first calibration data and the second calibration data to be described later. The first calibration data and the second calibration data are appropriately updated depending on the determination result of the determination unit 23 as described above.

The correction unit 22b calculates the first calibration data at each imaging position of the X-ray source 12 to be described in detail later. As will be described later, the correction unit 22b also calculates the second calibration data.

The correction unit 22b has a position detecting function of detecting an image position of the marker 20 in the captured image, automatically detects the position of the marker image respectively from the first image and the second image captured at different positions of the X-ray tube, and uses the detected positions to create the first calibration data, and provides the detected positions to the determination in the determination unit 23 on whether to update the first calibration data.

The determination unit 23 calculates an assumed position of a corresponding marker image which corresponds to the marker image in the second image based on the position of the marker image detected from the first image and the first calibration data, compares the calculated position with the position of the marker image detected in the second image, and calculates a misalignment amount therebetween. By comparing the misalignment amount with a predetermined threshold value, it is determined whether to update the calibration data.

The correction unit 22b calculates the first calibration data and updates the calibration data depending on the above-mentioned determination result of the determination unit 23 on whether to update the calibration data.

With respect to the first calibration data, when the determination unit 23 determines that it is necessary to perform calibration, the correction unit 22b creates first calibration data using at least two images captured while causing the X-ray source 12 to move in the movement direction (y direction) through the use of the movement unit 14. For example, the first calibration data is created using the first image 40 and the second image 42, as illustrated in FIG. 3, similarly to the first embodiment.

In this case, if the movement direction (y direction) of the X-ray source 12 is parallel to the length direction (Y direction) of the FPD 18, the position of the marker 20 in the X direction perpendicular to the length direction (Y direction) of the FPD 18 is the same in the first image 40 and the second image 42. That is, the shift amount is zero.

On the other hand, if the X-ray source 12 moves in a state where the movement direction (y direction) of the X-ray source 12 departs in the $y_\theta$ direction from the length direction of the FPD 18, for example, as illustrated in FIG. 2, similarly to the first embodiment, the position of the image of the marker 20 in the X direction is different, for example, by δ (that is, shift amount δ) between the first image 40 and the second image 42.

The misalignment angle θ (first slope) of the X-ray source 12 can be calculated on the basis of the shift amount δ and the distance d between the imaging positions of the first image 40 and the second image 42. That is, the misalignment angle θ can be calculated by $\theta = \tan^{-1}(\delta/d)$.

The correction unit 22b creates first calibration data on the basis of the misalignment angle θ (first slope) and stores the created first calibration data in the storage unit 22a.

The first calibration data is the position information of the X-ray source 12 (position information of the X-ray tube) for correction to information close to the actual position of the X-ray source 12 by correcting the slope of the movement axis of the X-ray source 12, for example, by the misalignment angle θ on the basis of designed values (target values indicating from what positions plural images are captured, respectively). The misalignment in the $y_\theta$ direction illustrated in FIG. 2 can be corrected using the first calibration data.

Similarly to the first embodiment, as illustrated in FIG. 4, the first image 40 and the second image 42 may be synthesized with the edges in the X direction of the captured images fitted to each other to acquire a synthesis image 44, the shift amount δ of the marker 20 may be calculated on the basis of the outer edge 44a of the synthesis image 44, and the misalignment angle θ (first slope) of the X-ray source 12 may be calculated on the basis of the shift amount δ and the distance d between the imaging positions of the first image 40 and the second image 42. In this way, the misalignment angle θ (first slope) of the X-ray source 12 can be calculated using the relative relationship between the positions of the captured images of the marker 20. The first calibration data may be created on the basis of the misalignment angle θ (first slope).

Since the misalignment angle θ (first slope) is the same as described in the first embodiment, detailed description thereof will not be repeated.

Regarding the misalignment amount of the distance between the X-ray source 12 and the surface 18a of the FPD 18 (X-ray source-FPD distance L), when the X-ray source-FPD distance L varies from the set distance, the size of the marker 20 in the captured image varies. Accordingly, in this embodiment, for the misalignment amount in the X-ray source-FPD distance L, the size of the marker 20 in the captured images and a variation rate of the marker 20 in the captured images that is, the size of the marker 20 and an enlargement rate or a reduction rate of the marker 20 at each distance L are calculated and are stored, for example, in the storage unit 22a. Further, the threshold values of the size of the marker 20 and the enlargement rate or the reduction rate of the marker 20 in the captured images are set and the threshold values are stored in the storage unit 22a.

The correction unit 22b may automatically detect the size of the marker image from the first image and the second image captured at different positions of the X-ray tube in addition to the position of the image of the marker 20, and may use the detected sizes to create the second calibration data, and may provide the detected sizes to the determination in the determination unit 23 on whether to update the second calibration data.

In this case, the determination unit 23 calculates the size of the image of the marker 20 in the first image 40 and the size of the image of the marker 20 in the second image 42. The determination unit 23 calculates the size of a corresponding marker image which corresponds to the marker image in the second image 42 from the second calibration data and compares the calculated size of the corresponding marker image with the size of the marker 20 in the second image 42 to calculate a misalignment amount. By comparing the calculated misalignment amount with a predetermined threshold value, it is determined whether to update the calibration data. The diameter difference between the images of the marker 20, the enlargement rate or the reduction rate of the images of the marker 20, and the like can be used as the misalignment amount.

With respect to the second calibration data, when the determination unit 23 determines that it is necessary to perform calibration, the correction unit 22b creates second calibration data using at least two images captured while causing the X-ray source 12 to move in the movement direction (y direction) through the use of the movement unit 14.

Figures 5A, 5B:
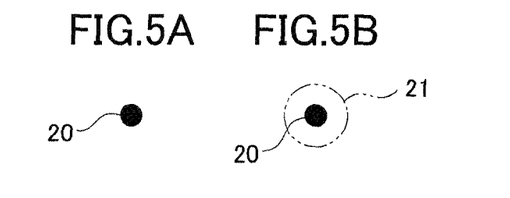
FIGS. 5A and 5B are schematic diagrams illustrating a variation of a marker image of a marker captured by the X-ray imaging device according to the first embodiment of the present invention.

For example, when the size of the marker 20 illustrated in FIG. 5A is changed to the marker 21 illustrated in FIG. 5B as the imaging result at two imaging positions, similarly to the first embodiment, the correction unit 22b can obtain the X-ray source-FPD distance L at each imaging position. Further, the correction unit 22b can calculate a misalignment angle (second slope) of the X-ray source 12 illustrated in FIG. 7 in a plane perpendicular to the surface of the FPD 18 on the basis of the distance L at each imaging position and the distance d between the imaging positions. In this way, the misalignment angle (second slope) of the X-ray source 12 in the z direction can be calculated using the relative relationship of the positions of the marker 20 in the captured images.

The correction unit 22b creates the second calibration data on the basis of the misalignment angle (second slope) and stores the created second calibration data in the storage unit 22a.

An example of the second calibration data is enlargement rate data or reduction rate data for enlarging or reducing the entire projection data by a value corresponding to the enlargement rate or the reduction rate so as to match the size of the marker 20 with the designed size. It is possible to correct the misalignment in the z direction illustrated in FIG. 7 using the second calibration data.

The threshold value for determining the degree of coincidence between the positions of the images of the marker 20 and the threshold value for determining the degree of coincidence between the sizes of the images of the marker 20 in the determination unit 23 may be set, for example, through the use of the input unit 28. Moreover, the calibration data (the first calibration data and the second calibration data) created by the correction unit 22b may also be set, for example, through the use of the input unit 28.

In this embodiment, the first calibration data and the second calibration data may be calculated for each position of the X-ray source 12, may be stored, for example, in the form of a table in the storage unit 22a, and may be used to perform the tomosynthesis imaging operation.

The reconstruction unit 22c performs an image synthesis processing on the plural pieces of projection data of the X-ray images including the projection data, which has been subjected to the correction processing if necessary by the correction unit 22b, using the position information of the X-ray source 12 (position information of the X-ray tube) corrected if necessary and reconstructs an X-ray tomographic image of a cross section of the subject M at an arbitrary height.

It is preferable that the correction unit 22b creates the first calibration data and the second calibration data, but the correction unit has only to create at least the first calibration data. By using at least the first calibration data out of the first calibration data and the second calibration data, it is possible to obtain a high-precision tomosynthesis image, and by using both the first calibration data and the second calibration data, it is possible to obtain a higher-precision tomosynthesis image. Accordingly, when an X-ray tomographic image of a cross section of the subject M at an arbitrary height is reconstructed by the reconstruction unit 22c, at least the position information of the X-ray source 12 (position information of the X-ray tube) corrected using the first calibration data by the correction unit 22b is used.

Also in this embodiment, the image processing unit 22 (the storage unit 22a, the correction unit 22b, and the reconstruction unit 22c) is not limited to hardware (device). For example, it may be implemented by a program causing a computer to perform the processing to be performed on the projection data stored in the storage unit 22a by the correction unit 22b and the reconstruction unit 22c of the image processing unit 22.

The display unit 24 has the same configuration as in the first embodiment and further serves as a notification unit that notifies the determination result of the determination unit 23 on whether to update the calibration data. The determination result of the determination unit 23 on whether to update the calibration data is displayed on the display unit 24, for example, in the form of characters under the control of the control unit 30.

In the tomosynthesis imaging using the X-ray imaging device 10a according to this embodiment, as described above, precise alignment of the FPD 18 (X-ray detector 18) and the movement axis of the X-ray source 12 is required. In the X-ray imaging device 10a using the overhead traveling X-ray source 12 as in this embodiment, since the X-ray source 12 and the FPD 18 are not integrated as a unified body, it is difficult to precisely align the X-ray source 12 and the FPD 18. Accordingly, when the X-ray source 12 moves, the X-ray source 12 may move in the $y_\theta$ direction departing from the length direction (Y direction) of the FPD 18 as illustrated in FIG. 2 and the reconstruction may be performed using the captured images obtained in that state. In this case, a high-precision synthesis image (tomosynthesis image) cannot be obtained. Even though the calibration is performed, the calibration data may not be appropriate due to aging degradation (aging variation).

However, in this embodiment, it is determined whether to update the calibration data as illustrated in FIG. 8, thereby suppressing an influence caused by aging degradation (aging variation) of the calibration data.

It is preferable that the calibration of the X-ray imaging device 10a be performed in a state where a subject M (patient) is not present on the surface 16a of the imaging platform 16, but the calibration may be performed in a state where a subject M (patient) is present thereon.

In FIG. 8, the calibration is already performed on the X-ray imaging device 10a and the first calibration data and the second calibration data are stored as initial calibration data in the storage unit 22a (step S10).

Then, before performing a tomosynthesis imaging operation on the subject M, for example, at the time of starting up the device, the X-ray source 12 is caused to move to at least two imaging positions through the use of the movement unit 14, the FPD 18 is irradiated with X-rays from the X-ray source 12 at each imaging position so as to image the marker 20, and image data including at least two captured images (for example, the first image 40 and the second image 42) including the marker 20 is output from the FPD 18 to the storage unit 22a of the image processing unit 22.

Then, the correction unit 22b calculates, for example, the position of the image of the marker 20 in the first image 40 and the position of the image of the marker 20 in the second image 42. Further, the determination unit 23 calculates the position of a corresponding image of a marker which corresponds to the image of the marker 20 in the second image 42 using the first calibration data currently stored. Then, the correction unit 22b calculates a misalignment amount between the position of the image of the marker 20 in the second image 42 and the position of the corresponding image of the marker obtained using the first calibration data (step S12).

Then, the misalignment amount at the position of the image of the marker 20 is output to the determination unit 23.

Then, the determination unit 23 determines whether to update the calibration data (to create the first calibration data) on the basis of the threshold value regarding the misalignment amount at the position of the image of the maker 20 stored in the storage unit 22a (step S14). The determination result on whether to create first calibration data is displayed, for example, in the form of characters or the like on the display unit 24 and is notified to a user or the like.

When it is determined in step S14 that the misalignment amount at the position of the image of the marker 20 is less than the threshold value, the first calibration data stored in the storage unit 22a is used to reconstruct an X-ray tomographic image without updating the initial calibration data.

On the other hand, when it is determined in step S14 that the misalignment amount at the position of the image of the marker 20 is greater than the threshold value, the first calibration data is created again (step S18).

In step S12, for example, the size of the image of the marker 20 in the first image 40 and the size of the image of the marker 20 in the second image 42 are calculated. Further, the determination unit 23 calculates the size of a corresponding image of a marker which corresponds to the image of the marker 20 in the second image 42 is calculated using the second calibration data currently stored. Then, the correction unit 22b may calculate the misalignment amount between the size of the image of the marker 20 in the second image 42 and the size of the corresponding image of the marker obtained using the second calibration data (step S12).

In this case, next, the misalignment amount between the sizes of the images of the marker 20 is output to the determination unit 23. The determination unit 23 determines whether to update the calibration data (to create second calibration data) on the basis of the threshold value regarding the misalignment amount between the sizes of the images of the marker 20 stored in the storage unit 22a (step S14). The determination result on whether to create the second calibration data is displayed, for example, in the form of characters or the like on the display unit 24 and is notified to a user or the like.

When it is determined in step S14 that the misalignment amount between the sizes of the images of the marker 20 is less than the threshold value, the second calibration data stored in the storage unit 22a is used to reconstruct an X-ray tomographic image without updating the initial calibration data.

On the other hand, when it is determined in step S14 that the misalignment amount between the sizes of the images of the marker 20 is greater than the threshold value, the second calibration data is created again (step S18).

The method of creating the first calibration data and the second calibration data is a method of capturing images including the marker 20 from at least two imaging positions and using data of the captured images as described above, and detailed description of the creating method will not be repeated.

Then, the first calibration data and the second calibration data stored as the initial calibration data in the storage unit 22a are replaced with the created first calibration data and the created second calibration data and the resultant calibration data is stored in the storage unit 22a. That is, the initial calibration data is updated (step S20).

In this way, it is determined whether to update the initial calibration data and the initial calibration data is updated on the basis of the determination result. Accordingly, even when the movement direction of the X-ray source 12 is out of alignment due to aging variation and the initial calibration data temporally degrades (temporally varies), appropriate calibration data can be used.

In this embodiment, for example, even when the movement axis of the X-ray source 12 is not straight, that is, even when the movement axis of the X-ray source 12 is out of alignment such as when the rail 13 is not parallel to the length direction (Y direction) of the FPD 18 (when the movement direction (y direction) of the X-ray source 12 is not parallel to the pixel arrangement direction of the FPD 18), it is possible to correct the misalignment, to always precisely reconstruct a tomosynthesis image using appropriate calibration data while suppressing the influence of the aging variation due to the misalignment of the movement axis of the X-ray source 12, and to always obtain a high-precision synthesis image (tomosynthesis image) of a cross section of a subject at a predetermined position.

Next, the tomosynthesis imaging of the X-ray imaging device 10a will be described below.

First, when an imaging start instruction is given from the input unit 28 after a subject M is positioned on the surface 16a of the imaging platform 16, the tomosynthesis imaging is started under the control of the control unit 30.

When the imaging is started, the subject M is irradiated with X-rays at different irradiation angles while causing the X-ray source 12 to move in the y direction through the use of the movement unit 14 and changing the emitting angle of the X-ray source 12 toward the subject M at a predetermined imaging position, and plural pieces of projection data (X-ray images) having different imaging angles are obtained by one time of imaging operation. When an X-ray image of the subject M is captured, the projection data corresponding to the captured X-ray image is output from the FPD 18 to the storage unit 22a of the image processing unit 22 and the plural pieces of projection data of the X-ray images acquired by the FPD 18 are stored in the storage unit 32.

The first calibration data and the second calibration data, for example, at each imaging position are stored in advance in the storage unit 22a. As in the method illustrated in FIG. 8, whether to update the calibration data is determined before the imaging, and the calibration data is updated depending on the determination result. The determination result on whether to update the calibration data is displayed, for example, in the form of characters or the like on the display unit 24.

Then, with respect to an imaging position having a position misalignment, the correction unit 22b corrects the imaging position (position information of the X-ray source 12 (position information of the X-ray tube)) in the projection data on the basis of the first calibration data and the second calibration data. The corrected imaging position (position information of the X-ray source 12 (position information of the X-ray tube)) is output to the reconstruction unit 22c.

Then, the reconstruction unit 22c reconstructs an X-ray tomographic image of a cross section at an arbitrary height of the subject M using the projection data and the corrected imaging position (position information of the X-ray source 12 (position information of the X-ray tube)). Since the position misalignment of the imaging position is corrected in this way, it is possible to obtain a high-precision synthesis image (tomosynthesis image) of a cross section at a predetermined position of the subject M.

For example, the obtained tomosynthesis image (X-ray tomographic image) is displayed on the display unit 24. The tomosynthesis image (X-ray tomographic image) is output to the output unit 26 and, for example, the output unit 26 prints out the tomosynthesis image (X-ray tomographic image) and stores digital image data of the X-ray tomographic image in a recording medium.

The reconstruction of an X-ray tomographic image in the tomosynthesis imaging according to this embodiment is carried out using the same method as the reconstruction according to the first embodiment and thus details thereof will not be repeated.

The present invention basically has the above-mentioned configuration. While the X-ray imaging device and the calibration method therefor according to the present invention have been described in detail, the present invention is not limited to the above-mentioned embodiments and may be improved or modified in various forms without departing from the gist of the present invention.

What is claimed is:
1. An X-ray imaging device comprising:
   an X-ray source that is able to move along a predetermined movement path;
   a movement unit configured to cause the X-ray source to move along the predetermined movement path;
   an imaging platform that is disposed to face the X-ray source;
   a flat-panel X-ray detector that is provided to the imaging platform;

a marker that is disposed in the imaging platform;
a control unit that causes the X-ray source to move via the movement unit and to capture images respectively including the marker from at least two positions; and
an image processing unit that calculates a position of an image of the marker in each of the captured images and corrects the each of the captured image using the slope of a movement axis of the X-ray source with respect to the X-ray detector and calculates a slope of a movement axis of the X-ray source with respect to the X-ray detector based on a relative relationship between positions of images of the marker.

2. The X-ray imaging device according to claim 1, wherein the slope with respect to the X-ray detector is a first slope in a plane parallel to a surface of the X-ray detector.

3. The X-ray imaging device according to claim 1, wherein the image processing unit further calculates a variation in size of an image of the marker in each of the captured images, calculates a distance between the X-ray source and the X-ray detector using the variation in size, and calculates a second slope in a plane perpendicular to a surface of the X-ray detector as another slope with respect to the X-ray detector.

4. The X-ray imaging device according to claim 1, wherein the image processing unit calculates the slope with respect to the X-ray detector for each imaging position of the X-ray source.

5. The X-ray imaging device according to claim 1, wherein the image processing unit has a function of reconstructing a tomographic image using a plurality of images obtained by causing the X-ray source to move to predetermined imaging positions via the movement unit and performing a tomosynthesis imaging operation, and
wherein the image processing unit uses the slope with respect to the X-ray detector to reconstruct the tomographic image.

6. A calibration method of an X-ray imaging device including an imaging platform disposed to face an X-ray source that is able to move along a predetermined movement path, a flat-panel X-ray detector provided to the imaging platform, and a marker, the calibration method comprising the steps of:
causing the X-ray source to move and to capture images respectively including the marker from at least two positions; and
calculating a position of an image of the marker in each of the captured images and calculating a slope of a movement axis of the X-ray source with respect to the X-ray detector based on a relative relationship between positions of images of the marker and corrects the each of the captured image using the slope of a movement axis of the X-ray source with respect to the X-ray detector.

7. The calibration method according to claim 6, wherein the slope with respect to the X-ray detector is a first slope in a plane parallel to a surface of the X-ray detector.

8. The calibration method according to claim 6, further comprising a step of calculating a variation in size of the marker image in each of the captured images, calculating a distance between the X-ray source and the X-ray detector using the variation in size, and calculating a second slope in a plane perpendicular to a surface of the X-ray detector as another slope with respect to the X-ray detector.

9. The calibration method according to claim 6, wherein the slope with respect to the X-ray detector is calculated for each imaging position of the X-ray source.

10. An X-ray tomosynthesis imaging device comprising:
an X-ray source that is able to move along a predetermined movement path;
a movement unit configured to cause the X-ray source to move along the predetermined movement path;
an imaging platform that is disposed to face the X-ray source;
a flat-panel X-ray detector that is provided to the imaging platform;
a marker that is disposed in the imaging platform;
a control unit that causes the X-ray source to move via the movement unit and to capture a plurality of first images respectively including the marker from a plurality of different positions and causes the X-ray source to move via the movement unit to a predetermined plurality of imaging positions via the movement unit to perform a tomosynthesis imaging operation and capture a plurality of second images by;
a storage unit that stores existing calibration data;
a calibration unit that performs a calibrating operation on a misalignment in a movement direction of the X-ray source disposed to face the X-ray detector;
and calculates a position of an image of the marker in each of the captured the plurality of the first images, and creates first calibration data based on a relative relationship between positions of images of the marker;
a determination unit that determines whether to update the existing calibration data stored in the storage unit to the first calibration data based on a position of an image of the marker in each of the captured the plurality of the first images,
a reconstruction unit that, when update is negative by the determination unit, reconstructs a tomographic image using the existing calibration data and the plurality of the second images, and, when update is positive by the determination unit, reconstructs a tomographic image using the first calibration data and the plurality of the second images.

11. The X-ray tomosynthesis imaging device according to claim 10, wherein the determination unit determines whether to update the calibration data based on a position of the first image of the marker and a position of the second image of the marker, the first image and the second image being two images in the plurality of the first images and determines whether to update the calibration data based on a misalignment between the position of the image of the marker in the second image and the position of the corresponding marker image which corresponds to the image of the marker in the second image.

12. The X-ray tomosynthesis imaging device according to claim 10, wherein the calibration unit calculates a first slope of a movement axis of the X-ray source in a plane parallel to the surface of the X-ray detector based on a relative relationship between a position of the image of the marker in the first image and a position of the image of the marker in the second image, and creates the first calibration data based on the first slope, and
wherein the first image and the second image are two images in the plurality of the first images.

13. The X-ray tomosynthesis imaging device according to claim 10, wherein the calibration unit calculates at least one variation in size of an image of the marker of the plurality of the first images, calculates a distance between the X-ray source and the X-ray detector using the variation in size, calculates a second slope of the X-ray source in a plane perpendicular a the surface of the X-ray detector, and creates second calibration data based on the second slope.

14. The X-ray imaging device according to claim 12, wherein the calibration unit calculates at least the first calibration data out of the first calibration data and the second calibration data for each imaging position of the X-ray source.

15. The X-ray imaging device according to claim 13, further comprising a reconstruction unit that reconstructs a tomographic image using a plurality of images obtained by causing the X-ray source to move to predetermined imaging positions via the movement unit and performing a tomosynthesis imaging operation,
wherein the reconstruction unit uses at least the first calibration data out of the first calibration data and the second calibration data to reconstruct the tomographic image using the plurality of images captured through the tomosynthesis imaging operation.

16. A calibration method of an X-ray tomosynthesis imaging device including an imaging platform disposed to face an X-ray source that is able to move along a predetermined movement path, a flat-panel X-ray detector provided to the imaging platform, and a marker, the calibration method comprising the steps of:
causing the X-ray source to move to capture a plurality of first images respectively including the marker from a plurality of different positions;
causing the X-ray source to move to a plurality of predetermined imaging positions and perform a tomosynthesis imaging operation to capture a plurality of second images;
calculating a position of an image of the marker in each of the plurality of the first images captured, and creating first calibration data based on a relative relationship between positions of images of the marker,
determining whether to update the existing calibration data based on a position of an image of the marker in each of the plurality of the first images captured, and
when update is rejected, reconstructing a tomographic image using the existing calibration data and the plurality of the second images, and, when update is approved, reconstructing a tomographic image using the first calibration data and the plurality of the second images.

17. The calibration method of an X-ray tomosynthesis imaging device according to claim 16, wherein the step of performing the calibration includes steps of:
determines whether to update the calibration data based on a position of the first image of the marker and the position of the second image, the first image and the second image being two images in the plurality of the first images;
calculating a position of a corresponding marker image which corresponds to the image of the marker in the second image from the position of the image of the marker in the first image using existing calibration data; and
determining whether to update the calibration data based on a misalignment between the position of the image of the marker in the second image and the position of the corresponding marker image which corresponds to the image of the marker in the second image.

18. The calibration method of an X-ray tomosynthesis imaging device according to claim 16, wherein the step of performing the calibration includes steps of:
calculating a first slope of a movement axis of the X-ray source in a plane parallel to a surface of the X-ray detector based on a relative relationship between a position of images of the marker in the first image and a position of images of the marker in the second image; and
creating the first calibration data based on the first slope, the first image and the second image being two images in the plurality of the first images.

19. The calibration method an X-ray tomosynthesis imaging device according to claim 16, wherein the steps of calculating at least one variation in size of an image of the marker of the plurality of the first images, calculates a distance between the X-ray source and the X-ray detector using the variation in size, calculates a second slope of the X-ray source in a plane perpendicular to a surface of the X-ray detector, and creates second calibration data based on the second slope.

* * * * *